United States Patent
Fargahi

(10) Patent No.: US 8,870,854 B2
(45) Date of Patent: Oct. 28, 2014

(54) RELEASE DEVICE FOR DETACHING A MEDICAL IMPLANT FROM AN INSERTION DEVICE AND AN INSERTION DEVICE COMPRISING A RELEASE DEVICE

(71) Applicant: Biotronik AG, Buelach (CH)

(72) Inventor: Amir Fargahi, Buelach (CH)

(73) Assignee: Biotronik AG, Buelach (CH)

( * ) Notice: Subject to any disclaimer, the term of this patent is extended or adjusted under 35 U.S.C. 154(b) by 139 days.

(21) Appl. No.: 13/681,310

(22) Filed: Nov. 19, 2012

(65) Prior Publication Data

US 2013/0138084 A1      May 30, 2013

Related U.S. Application Data

(60) Provisional application No. 61/563,556, filed on Nov. 24, 2011.

(51) Int. Cl.
*A61M 25/00* (2006.01)
*A61F 2/95* (2013.01)

(52) U.S. Cl.
CPC .... *A61M 25/0082* (2013.01); *A61F 2002/9517* (2013.01); *A61F 2/95* (2013.01)
USPC ................................ 606/1; 623/1.11; 604/528

(58) Field of Classification Search
CPC ........... A61F 2/06; A61B 17/00; A61M 25/00
USPC ................................ 606/1; 623/1.11; 604/528
See application file for complete search history.

(56) References Cited

U.S. PATENT DOCUMENTS

| | | | | |
|---|---|---|---|---|
| 5,776,142 | A | * | 7/1998 | Gunderson ................... 623/1.11 |
| 7,837,724 | B2 | * | 11/2010 | Keeble et al. ................ 623/1.11 |
| 2005/0080476 | A1 | | 4/2005 | Gunderson et al. |

FOREIGN PATENT DOCUMENTS

| | | |
|---|---|---|
| WO | 2008124844 A1 | 10/2008 |
| WO | 2010042950 A2 | 4/2010 |

OTHER PUBLICATIONS

European Search Report for 12190799.2.

* cited by examiner

*Primary Examiner* — William Thomson
*Assistant Examiner* — Victor Shapiro
(74) *Attorney, Agent, or Firm* — Wagenknecht IP Law Group PC

(57) ABSTRACT

A release device (100) and an insertion device (110) having such a release device (100) for detaching a medical implant from an insertion device (110), in which the implant can be released by way of a relative movement between a first and a second insertion element (52, 54), including a body (10) having a proximal end (12), which faces a user in the usage state, and a distal end (14), which is furthest away from a user in the usage state, wherein a spindle (10a) including at least two speed regions is provided between the proximal end and distal end (14), wherein the spindle (10a) is provided so as to generate a deliberate to relative movement between the first and second insertion elements (52, 54) of the insertion device (110).

15 Claims, 5 Drawing Sheets

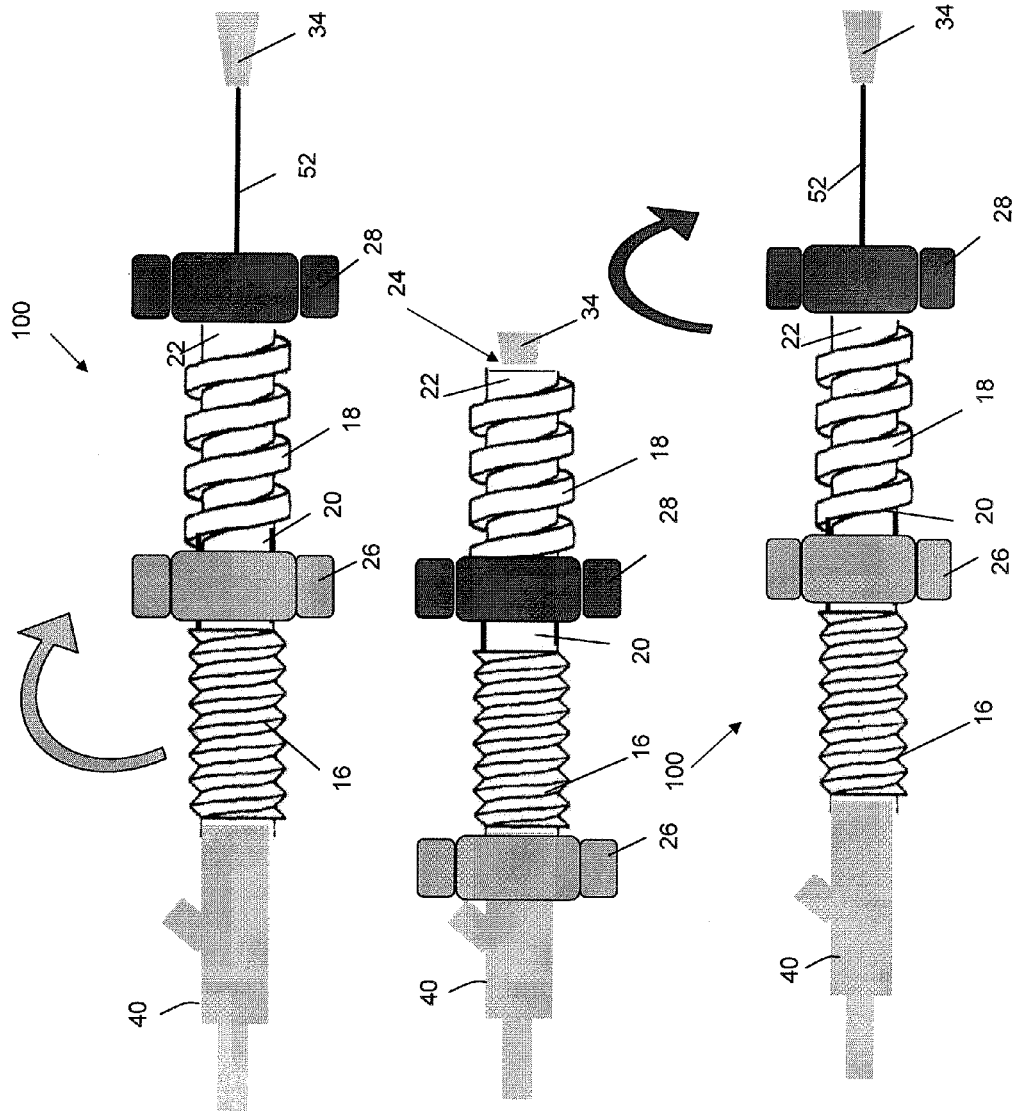

RELEASE DEVICE FOR DETACHING A MEDICAL IMPLANT FROM AN INSERTION DEVICE AND AN INSERTION DEVICE COMPRISING A RELEASE DEVICE

CROSS REFERENCE TO RELATED APPLICATIONS

This application claims benefit of priority to U.S. provisional patent application Ser. No. 61/563,556, filed Nov. 24, 2011; the content of which is herein incorporated by reference.

TECHNICAL FIELD

The invention relates to a release device for detaching a medical implant from a catheter and to a catheter having a release device for releasing a medical implant for implantation in an animal and/or human body.

BACKGROUND

In medicine, implants are frequently used which are introduced permanently, or at least for an extended period, into an animal and/or human body so as to fulfill replacement functions. These include, for example, cardiac pacemakers, brain pacemakers for patients with Parkinson's disease, cardiac implants, cochlear implants, retina implants, dental implant, implants for joint replacement, vascular prostheses or stents.

For insertion in the body, implants are connected to catheters and it must be possible to precisely place them at the site of use and release them in a defined manner. For this purpose it is known, for example, to release the implant using a sliding motion.

SUMMARY

It is the object of the invention to provide a release device which improves the deliberate release of an implant.

It is another object to provide a corresponding insertion device.

The invention includes a release device for detaching a medical implant from an insertion device, in which the implant can be released by way of a relative movement between a first and a second insertion element, including a body having a proximal end, which faces the user in the usage state, and a distal end, which is furthest away from the user in the usage state, wherein a spindle comprising at least two speed regions is provided between the proximal and distal ends, wherein the spindle is provided so as to generate a deliberate relative movement between the first and second insertion elements of the insertion device.

A simple switch can advantageously be made from a fast to a slow release, and conversely. For this purpose, mechanisms for switching from a fast to a slow release are provided. The invention allows for easy handling, notably switching between the speed regions. This makes it possible to easily, simply and quickly control the speed when releasing the implant. The release of the implant becomes more precise and faster.

According to an advantageous embodiment, the respective speed regions can be disposed along a longitudinal extension of the spindle. This allows for a compact and simple design of the release device.

According to an advantageous embodiment, the speed regions can be disposed behind one another along the longitudinal extension. The speed regions can be clearly arranged and are easy to activate.

According to an advantageous embodiment, an operating element can be associated with the respective speed region, this operating element cooperating with the respective speed region so as to effect the relative movement between the first and second insertion element of the insertion device. The respective speed region can notably have a thread, wherein the speed regions have thread pitches that differ from each other. Advantageously, the respective operating element may comprise an actuating element, which protrudes from the housing. The operating element can particularly advantageously comprise a nut having a pitch that corresponds to the relevant speed region of the spindle. In the case of a nut drive, the rotational axis of the gear wheel is disposed parallel to the displacement direction of the spindle. This allows two different speed regions of the release device to be implemented in a simple manner. High precision in positioning the implant can be achieved by use of the nuts, instead of employing sliding and retracting motions of the insertion elements as with the prior art.

The operating element can advantageously be fixed with respect to a housing, which is disposed at least around the spindle. The housing can be a handle of the insertion device for inserting a medical implant. The respective operating element can advantageously protrude from the housing, whereby it can be easily actuated from the outside.

According to a favorable embodiment, the operating element may comprise, at least in some regions, a thread which can be radially displaced, notably in the operating element. The radial displacement can be achieved in particular by a rotational movement of the operating element.

According to a further aspect of the invention, an insertion device is proposed for inserting a medical implant, which can be released by way of a relative movement between a first and a second insertion element, comprising a release device for detaching the medical implant, in particular according to any one of the preceding claims, comprising a body having a proximal end, which faces the user in the usage state, and a distal end, which is furthest away from the user in the usage state, wherein a spindle comprising at least two speed regions is provided between the proximal and distal ends, wherein the spindle is provided so as to generate a deliberate relative movement between the first and second insertion elements of the insertion device.

The insertion device can advantageously be a catheter. It is particularly advantageous when the insertion device is used to install and release a prosthesis, a heart valve or a stent.

According to a favorable embodiment, a sheath that is connected to an outer one of the insertion elements can be disposed at the distal end of the spindle. The spindle can notably be fixed to the sheath. This allows for a stable and sturdy design.

According to a favorable embodiment, an inner insertion element can be guided through the spindle. This allows for a compact construction of the insertion device.

DESCRIPTION OF THE DRAWINGS

The invention will be described in more detail hereafter by way of example based on exemplary embodiments shown in the drawings. In the drawings, shown in schematic illustrations:

FIGS. 3a to 3c are side views of the release device of FIG. 1 in various positions of the operating elements for a slow release of the implant.

DETAILED DESCRIPTION

Figure 1:
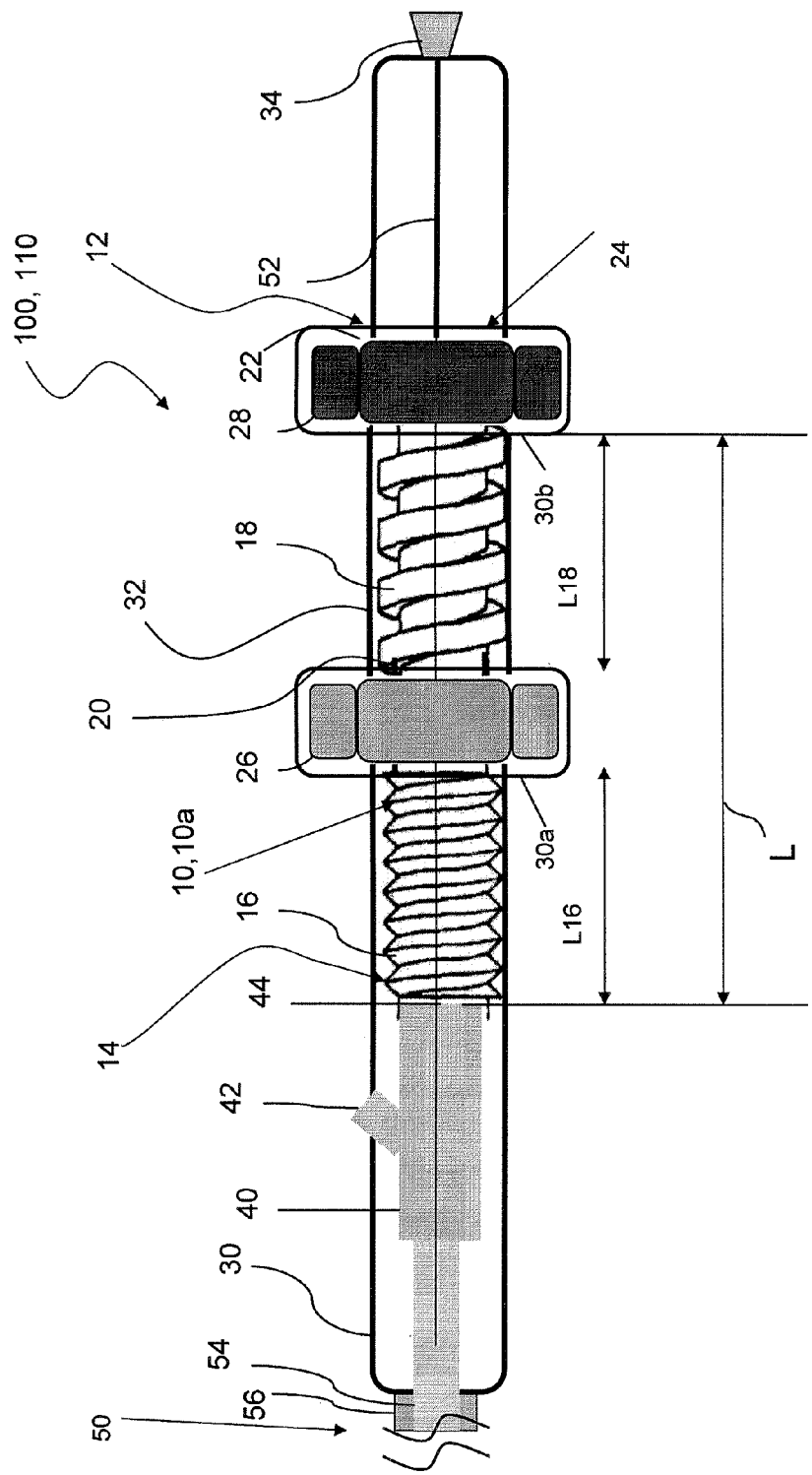
FIG. 1 is a side view of an embodiment of an insertion device and a release device according to the invention, comprising a cut-open housing.

In the figures, functionally equivalent or equivalently acting elements are denoted by the same reference numerals. The figures are schematic illustrations of the invention. They depict non-specific parameters of the invention. In addition, the figures only reflect typical embodiments of the invention and are not intended to limit the invention to the embodiments shown.

FIG. 1 is a schematic side view of a favorable embodiment of a detail of an insertion device 110 and a release device 100 according to the invention, comprising a cut-open housing 30 which forms a handle of the insertion device 110.

The insertion device 110 is, for example, a catheter comprising a shaft region 50 having two coaxially disposed insertion elements 52, 54, for example an inner shaft (insertion element 52) and an outer shaft (insertion element 54) which surrounds the inner shaft and can, in turn, be surrounded by an outer jacket 56. The insertion device 110 is shown only at the proximal end thereof, which faces a user. The implant (not shown) is typically placed at the distal end of the shaft region 50 between the inner shaft and outer shaft and should be released at the implantation site in the animal or human body.

The release device 100 is used to detach the medical implant from the insertion device 110. The implant is disposed at an end of the shaft region 50 which is located opposite of the housing 30. The implant is, for example, placed around the inner insertion element 52 and is released by a relative movement between the first and second insertion elements 52, 54.

The release device 100 comprises a body 10 having a proximal end 12, which faces a user in the usage state, and a distal end 14, which is furthest away from the user in the usage state. A spindle 10a, which comprises two speed regions 16, 18, extends between the two ends 12, 14. The first speed region 16 is used for a slow release and has a thread with a low pitch, while the second speed region 18 is used for a fast release and has a thread with a different, which is to say steeper, pitch. The spindle 10a is used to generate a deliberate relative movement between the first and second insertion elements 52, 54, which can be carried out quickly or slowly, depending on which speed region 16 or 18 is activated. The housing 30 can form the handle of the insertion device 110 and surrounds the spindle 10a and a sheath body 40 (also known as T-body). The sheath body 40 comprises a connector 42, for example in the form of a luer lock 42.

A matching operating element 26, 28, for example in the form of a screw nut, is provided for each of the speed regions 16, 18 present on the spindle 10a. The operating elements 26, 28 can be accessed from the outside through adapted housing regions 30a and 30b and are fixed with respect to the housing 30 in the longitudinal direction of the housing 30 in these housing regions 30a, 30b.

The inner insertion element 52 (inner catheter shaft) is fixed to the housing by means of a connector 34, for example in the form of a luer lock, wherein the insertion element 52 is guided through a passage 24 in the spindle 10a. The sheath body 40 is rigidly connected to the forward thread (speed region 16) at a fixation 44. Upon rotation of the respective operating element 26, 28, the outer shaft (insertion element 54) can be moved or displaced with respect to the inner shaft (insertion element 52) by moving the respective operating element 26, 28 achieved by a rotation about the spindle 10a along the axial extension L16, L18 of the respective speed region 16, 18. The length of each speed region 16, 18 is advantageously dimensioned such that it is at least as long as the length of the implant to be released.

Figure 2A:
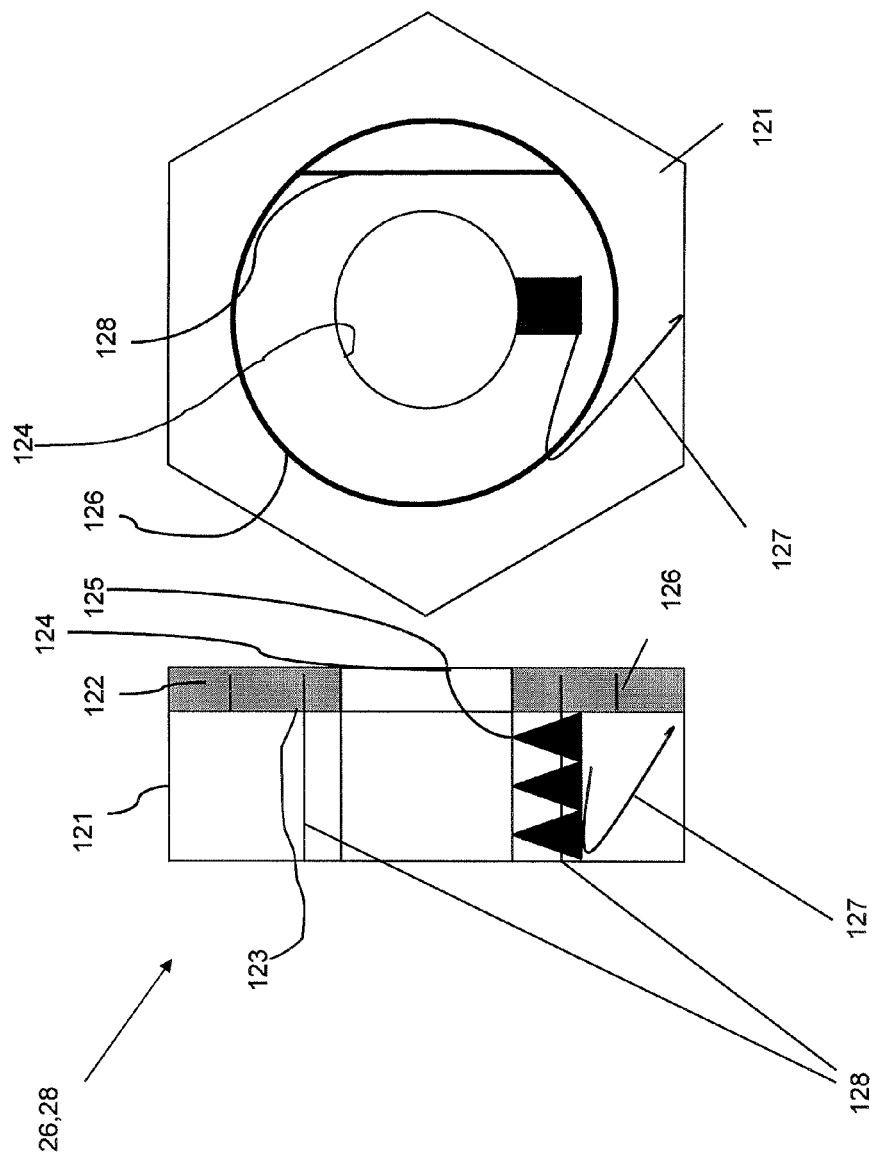
FIGS. 2a, 2b are a side view and a top view of a favorable embodiment of an operating element comprising a threaded piece in a deactivated state (FIG. 2a) and in the activated, radially inwardly displaced threaded piece (FIG. 2b)
Figure 2B:
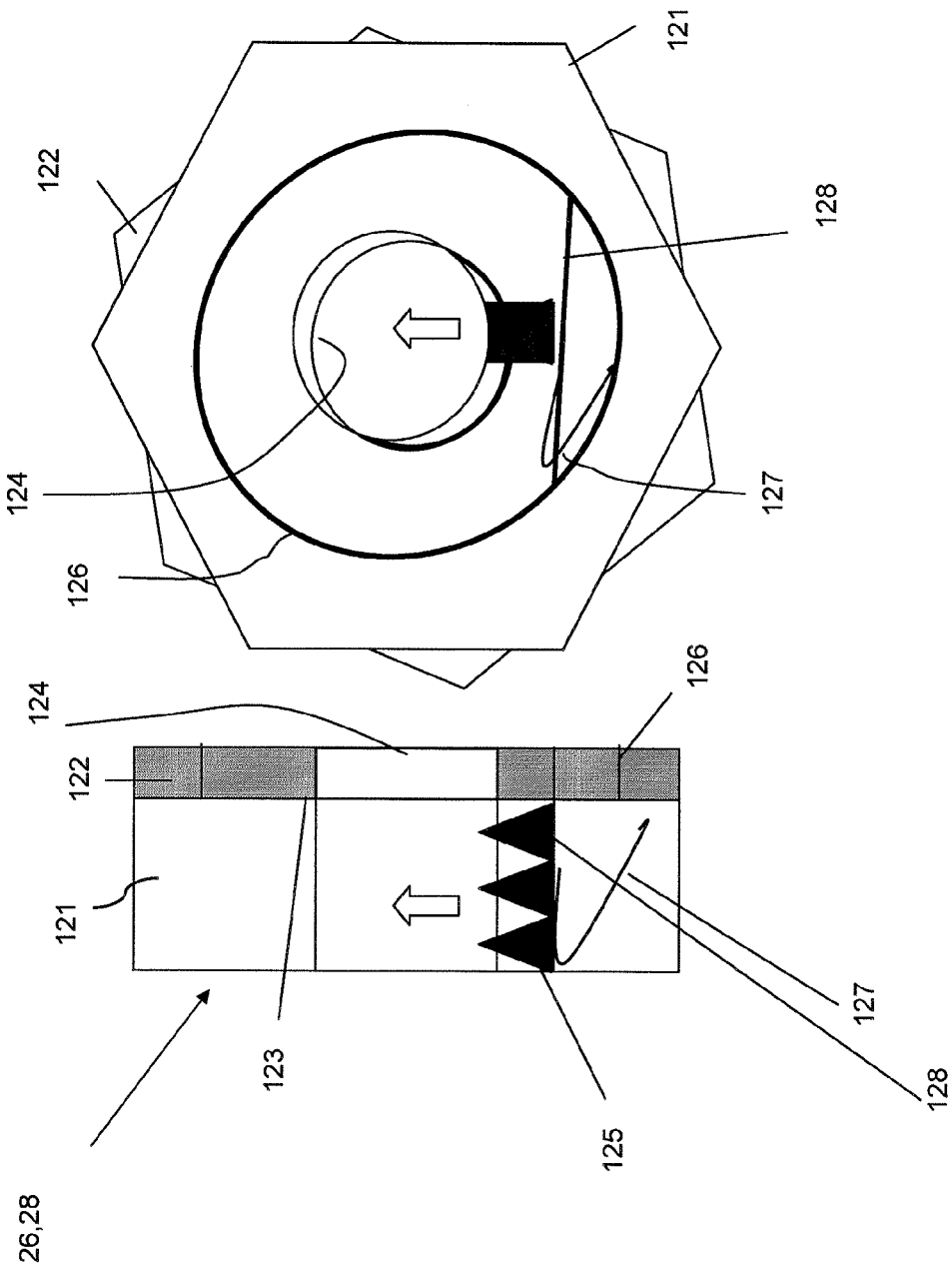

In the neutral position, the operating element 26 rests on a seat 20 and the operating element 28 rests on a seat 22. In the housing region 32, the operating elements 26, 28 protrude from the housing 30 and can be actuated from the outside, for example manually. The mechanisms of action of these elements are shown in more detail in FIGS. 2a and 2b.

Because two threads (speed regions 16, 18) and two nuts (operating elements 26, 28) are present, conflicts between the operating elements 26, 28 during the rotation can be avoided by deactivating one of the operating elements 26, 28. If, for example, the operating element 26 is rotated and moved along the speed region 16, the operating element 28 at the other speed region 18 must be deactivated or disengaged.

The operating elements 26, 28 are especially designed for this purpose. Each operating element 26, 28 is composed of two parts that are axially connected to each other and can be radially counter-rotated by means of a rotatable fixation 123. The first part is a body 121 comprising a region that has an internal thread 125. The internal thread 125 is associated with a (central) axial bore hole 124 in the body 121 and can be activated and disengaged (deactivated). The bore hole 124 is a through-hole for the spindle 10a (FIG. 1). The second part has an annular shape and comprises a flattened region 128 on the inner circumference 126. The second part forms a base 122 having no internal thread. The outer circumference of the two parts can be designed, for example, as a hexagon or have a different shape, for example a knurl or the like.

The diameter of the bore hole 124 is dimensioned such that, in the activated position, the respective speed region 16, 18 of the spindle 10a cooperates with the internal thread 125 substantially in the manner of a nut and screw.

The internal thread 125 is matched to the pitch of the thread of the respective speed region 16 or 18 and can extend peripherally around the bore hole 124 in some regions. In the exemplary embodiment shown, the internal thread 125 is configured only over a limited region of the inner circumference of the bore hole 124. The internal thread 125 substantially represents only a thread piece. A return spring 127 holds the internal thread 125 outside of the bore hole 124 in an idle position. The operating element 16, 18 is deactivated in this idle position.

The inside of the base 122 comprises a flattened region 128, which extends through the entire axial length of the body 121. When rotating the base 122 with respect to the body 121, the flattened region 128 ends up underneath the internal thread 125 such that this thread is pushed radially into the bore hole 124 by the flattened region 128, against the spring force of the return spring 127, and fixed in place there by the flattened region 128. The internal thread 125 is now in the activated state and can now mesh with the thread of the associated speed region 16, 18, whereby the insertion elements 52, 54 (FIG. 1) move axially with respect to each other when the body 121 is rotated with respect to the spindle 10a (FIG. 1). The flattened region 128 serves as a control surface for the radial movement of the internal thread 125. In the exemplary embodiment shown (FIG. 2b), the base 122 is rotated 90° so as to fully rotate the flattened region 128 underneath the internal thread 125 and introduce the internal thread 125 into the bore hole 124.

In order to deactivate the operating element 26, 28, the flattened region 128 is turned back, whereby the internal thread 125 is released radially, so that the return spring 127 moves the internal thread 125 radially outwardly again and reaches the idle position. During a rotation of the operating element 26, 28, the internal thread 125 can now no longer mesh with the corresponding thread of the speed region 16, 18. The operating element 26, 28 is now deactivated or disengaged.

If the insertion device is a catheter, with a stent as the implant, in practical experience the stent can initially be released at a slower speed, up to a certain length, and thus be positioned with great precision. Thereafter, the stent can be released fully at a higher speed.

Figure 4:
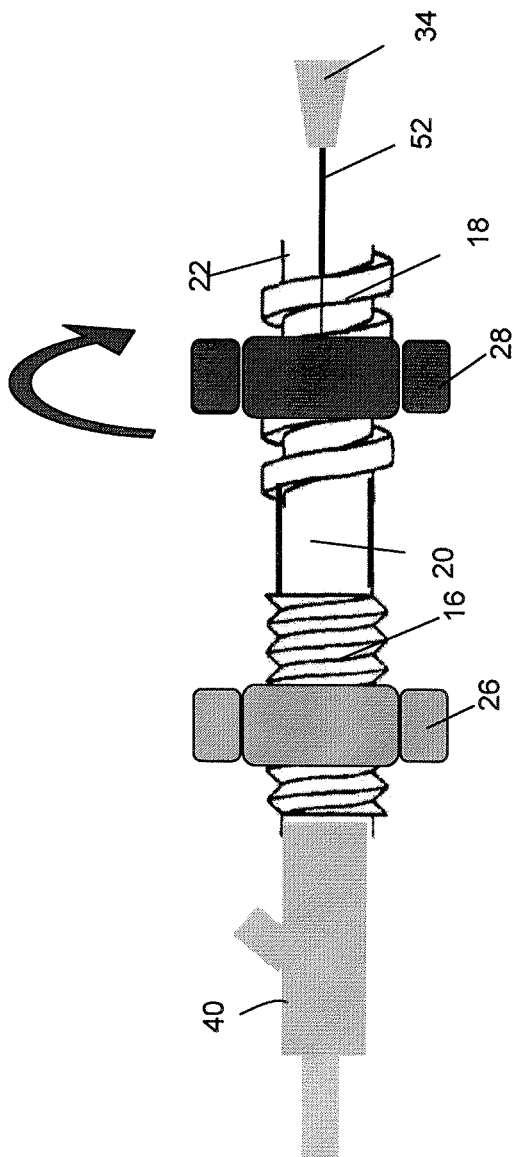
FIG. 4 is a side view of the release device of FIG. 1 in a position of the operating elements for a fast release of the implant.

FIGS. 3a to 3c show states of the release device 100, or positions of the operating elements 26, 28, during a slow release of the implant, and FIG. 4 shows a state or positions of the operating elements 26, 28 during a faster release of the implant.

For a slow release, which is to say so as to effect a slow relative movement of the two insertion elements 52, 54, first the operating element 26 must be activated, which is to say the appropriate internal thread must be moved radially inwardly, while the operating element 28 must be deactivated, which is to say in the neutral position the appropriate internal thread is positioned radially outside of the through-hole for the spindle 10a (FIG. 3a). When the operating element 26 is rotated about the spindle 10a (FIG. 3b), it moves slowly along the spindle 10a, given of the lower thread pitch of the speed region 16, until the desired segment of the implant has been released. The sense of rotation of the operating element 26 is, for example, clockwise, as indicated by a curved arrow over the operating element 26. If the entire implant is to be released slowly over the full length, the operating element 26 is rotated until it reaches the rinsing body 40 serving as a stop. Meanwhile, the deactivated operating element 28 slides on the spindle 10a without thread meshing.

The slow release is particularly suited for starting the release of the implant at the implantation site.

It is also possible to transition from a slow to a fast release. For this purpose, as in FIG. 3a, the operating element 26 is activated for a slow release of the implant, and the operating element 28 is deactivated. The operating element 26 is rotated about the spindle 10a until a desired portion of the total length L16 of the speed region 16 has been covered. Meanwhile, the operating element 28 is sliding over the spindle 10a in a function-less manner. The operating element 28 is then activated for a fast release of the implant, and the operating element 26 is deactivated. By rotating the operating element 28, a fast axial movement of the insertion elements 52, 54 now takes place (FIG. 1).

For a fast release, the operating element 28 is activated, which is to say the internal thread is moved radially inwardly, while the operating element 26 must be deactivated (FIG. 4). When the operating element 28 is rotated about the spindle 10a, the insertion elements 52, 54 move more quickly relative to each other than during the slower release because of the large thread pitch of the speed region 18 and are pulled apart quickly, whereby a fast release of the implant is effected.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release device for detaching a medical implant from an insertion device, in which the implant can be released by way of a relative movement between a first and a second insertion element, comprising a body having a proximal end, which faces a user in the usage state, and a distal end, which is furthest away from a user in the usage state, wherein a spindle comprising at least two speed regions is provided between the proximal and distal ends, each speed region having a different operating element so as to generate a deliberate relative movement between the first and second insertion elements of the insertion device by selectively operating the different operating elements.

2. The release device according to claim 1, wherein the respective speed regions are disposed along a longitudinal extension of the spindle.

3. The release device according to claim 1, wherein the speed regions are disposed behind one another along a longitudinal extension.

4. The release device according to claim 1, wherein the speed regions have thread pitches that are different for the different speed regions.

5. The release device according to claim 1, wherein the operating elements is are fixed with respect to a housing, which is disposed at least around the spindle.

6. The release device according to claim 5, wherein each operating element comprises an actuating element protruding from the housing.

7. The release device according to claim 1, wherein each operating element has a thread at least in some regions.

8. The release device according to claim 7, wherein the thread can be radially displaced in the operating element.

9. An insertion device for inserting a medical implant, which can be released by way of a relative movement between a first and a second insertion element, comprising a release device for detaching the medical implant, comprising a body having a proximal end, which faces a user in the usage state, and a distal end which is furthest away from a user in the usage state, wherein a spindle having at least two speed regions is provided between the proximal end and distal end, each speed region having a different operating element so as to generate a deliberate relative movement between the first and second insertion elements of the insertion device by selectively operating the different operating elements.

10. The insertion device according to claim 9, wherein a sheath, which is connected to an outer one of the insertion elements, is disposed at the distal end.

11. The insertion device according to claim 9, wherein the first insertion element is an inner insertion element that is guided through the spindle.

12. The insertion device according to claim 11, wherein the spindle is fixed to the sheath.

13. The insertion device according to claim 9, wherein the each operating element comprises at least one thread, which can be displaced radially in the operating element by means of an actuating element and which protrudes from a housing disposed at least around the spindle.

14. The release device according to claim 1, wherein the implant is slidably positioned between the first and second insertion elements.

15. The insertion device according to claim 9, wherein the implant is slidably positioned between the first and second insertion elements.

* * * * *